(12) United States Patent
Aga et al.

(10) Patent No.: US 8,447,084 B2
(45) Date of Patent: May 21, 2013

(54) CHROMATOGRAPHY INSPECTION APPARATUS AND METHOD FOR JUDGING DEGRADATION OF CHROMATOGRAPHY SPECIMEN

(75) Inventors: Masahiro Aga, Ehime (JP); Koji Miyoshi, Ehime (JP); Mie Takahashi, Ehime (JP); Hideyuki Kurokawa, Ehime (JP); Takahiko Tanida, Ehime (JP); Ryosuke Yamada, Ehime (JP); Yoko Matsuda, Ehime (JP)

(73) Assignee: Panasonic Corporation, Osaka (JP)

( * ) Notice: Subject to any disclaimer, the term of this patent is extended or adjusted under 35 U.S.C. 154(b) by 505 days.

(21) Appl. No.: 12/740,447

(22) PCT Filed: Oct. 14, 2008

(86) PCT No.: PCT/JP2008/002888

§ 371 (c)(1),
(2), (4) Date: Apr. 29, 2010

(87) PCT Pub. No.: WO2009/057252

PCT Pub. Date: May 7, 2009

(65) Prior Publication Data

US 2010/0260411 A1    Oct. 14, 2010

(30) Foreign Application Priority Data

Nov. 2, 2007   (JP) .................................. 2007-285616

(51) Int. Cl.
*G06K 9/00* (2006.01)
*G01N 21/84* (2006.01)
*G01N 33/543* (2006.01)

(52) U.S. Cl.
CPC ...... *G01N 21/8483* (2013.01); *G01N 33/54386* (2013.01)

USPC .......................... 382/128; 435/288.7; 356/244

(58) Field of Classification Search
None
See application file for complete search history.

(56) References Cited

U.S. PATENT DOCUMENTS

| 5,598,933 | A * | 2/1997 | Lessard et al. ................. 211/74 |
| 6,267,722 | B1 | 7/2001 | Anderson et al. |
| 7,192,784 | B2 | 3/2007 | Nadaoka et al. |
| 2003/0013206 | A1 | 1/2003 | Takahashi et al. |
| 2003/0054567 | A1 | 3/2003 | Miyoshi et al. |
| 2009/0093968 | A1 | 4/2009 | Kawamata et al. |

FOREIGN PATENT DOCUMENTS

| EP | 1249696 | 10/2002 |
| JP | 5-5736 | 1/1993 |
| JP | 2001-318100 | 11/2001 |
| JP | 2002-14097 | 1/2002 |
| JP | 2003-4743 | 1/2003 |
| JP | 2007-107889 | 4/2007 |
| WO | 2007/007849 | 1/2007 |

OTHER PUBLICATIONS

International Search Report of PCT/JP2008/002888, dated Dec. 22, 2008.

* cited by examiner

*Primary Examiner* — Barry Drennan
(74) *Attorney, Agent, or Firm* — Hamre, Schumann, Mueller & Larson, P.C.

(57) ABSTRACT

By measuring a luminance difference between predetermined two points or a luminance variation in a predetermined region in a state in which a liquid sample is developed in a chromatography specimen 1, and comparing the luminance difference or the luminance variation with a preset reference value, it is possible to automatically detect degradation such as a decrease in hydrophilicity in the lower portion of a liquid-impermeable sheet material 8 during a chromatography inspection, thereby enabling an accurate inspection.

8 Claims, 5 Drawing Sheets

CHROMATOGRAPHY INSPECTION APPARATUS AND METHOD FOR JUDGING DEGRADATION OF CHROMATOGRAPHY SPECIMEN

TECHNICAL FIELD

The present invention relates to a chromatography inspection apparatus for conducting an inspection by optically detecting a signal to measure a component concentration in a liquid sample, and a method for judging degradation of a chromatography specimen.

BACKGROUND ART

In recent years, home care and community care in a doctor's office, a clinic, and so on have developed and the number of early diagnoses and urgent clinical inspections has increased. Accordingly, there has been a demand for analyzers that enable non-professionals of clinical inspections to quickly conduct high-precision measurements for clinical inspections with ease. For this reason, analyzers for POCT (Point of Care Testing) have received attention because the analyzers can conduct reliable inspections in a short time without complicated operations. POCT is a generic name of inspections generally conducted in "locations near patients", for example, in the consulting rooms of practitioners and specialists, wards, and clinics for outpatients.

A dry-type biosensor such as a chromatography specimen using immune response does not require any adjustments of a reagent and enables an analysis of a target analyte in a liquid sample such as blood and urine only with a simple operation such as dropping of the liquid sample to be inspected. Thus many dry-type biosensors have been put into practical use as typical POCT.

Referring to FIG. 5, the following will describe the configuration and inspecting operation of an immunochromatography specimen according to the prior art.

FIG. 5 is a perspective view showing the configuration of the chromatography specimen according to the prior art.

In FIG. 5, reference numeral 1 denotes a specimen for chromatography (hereinafter called a specimen) and reference numeral 2 denotes a support that supports a chromatography material and is made of a plastic and the like. Reference numeral 3 denotes a developing layer that develops a liquid sample and is made of nitrocellulose and the like. Reference numeral 4 denotes a sample adding part for adding or applying the liquid sample. Reference numeral 5 denotes a labeling reagent retaining part for retaining a labeling reagent that is disposed so as to be melted by the development of a sample on the developing layer. Reference numeral 6 denotes a reagent fixing part for fixing a reagent such as specific protein on a region of the developing layer 3. Reference numeral 7 denotes a water absorbing part for absorbing the liquid sample in the end. Reference numeral 8 denotes a transparent liquid-impermeable sheet material that is made up of plastic tape and the like. The liquid-impermeable sheet material 8 tightly covers a part of the specimen 1 except for end regions upstream and downstream of the specimen 1. The labeling reagent retaining part 5, the reagent fixing part 6, and the water absorbing part 7 are each configured as a part of the developing layer 3.

The operations of the specimen 1 configured thus will be described below.

First, a liquid sample added to the sample adding part 4 starts developing the developing layer 3 and reaches the region of the labeling reagent retaining part 5. Next, a labeling reagent retained in the region of the labeling reagent retaining part 5 is melted by the development of the liquid sample and develops downstream of the developing layer 3 along with the liquid sample. The reagent fixing part 6 is provided on the developing layer 3. When the liquid sample contains a target analyte, specific protein fixed in the reagent fixing part 6 causes a combination reaction with a composite of the target analyte and the labeling reagent and a color reaction occurs in the region of the reagent fixing part 6, whereas when the liquid sample does not contain the target analyte, a combination reaction or a color reaction does not occur. Finally, the liquid sample develops to the water absorbing part 7 in the extreme downstream region of the developing layer 3, so that the operation of the specimen 1 is completed.

At this point, at least a measurement region is tightly covered with the liquid-impermeable sheet material 8 made up of transparent plastic tape and the like, thereby preventing water evaporation. The measurement region ranges from the labeling reagent retaining part 5 located upstream of a surface of the developing layer 3 to the reagent fixing part 6 located downstream of the labeling reagent retaining part 5. Further, the liquid-impermeable sheet material 8 makes it possible to evenly develop the liquid sample over the measurement region and keep constant the concentrations of the liquid sample and the labeling reagent that pass through the measurement region for a certain period of time, so that a chromatography inspection can be conducted with accuracy.

In the case where the labeling reagent is gold colloid particles, a color reaction becomes visible in the reagent fixing part 6, so that the result of a qualitative judgment can be obtained by visual observation. When a semiquantitative or quantitative measurement is necessary with precision, the concentration of the target analyte in the liquid sample can be detected by a method of reading reflection absorbance by using a reflectance spectrophotometer. Further, the concentration of the target analyte can be detected by a method of capturing a coloration result of the specimen 1 as an image by an image pickup device such as a camera and performing arithmetic processing.

Patent Document 1: Japanese Patent Laid-Open No. 2002-14097

DISCLOSURE OF THE INVENTION

Problems to be Solved by the Invention

However, in the case where the specimen configured thus expires or the specimen has been stored, even before the expiration date, under an adverse environment not conforming to the specifications, an adhesive for bonding the liquid-impermeable sheet material 8 to the developing layer 3 permeates the upper portion of the developing layer 3 and causes degradation that is reduced hydrophilicity. At this point, when a user uses the specimen without noticing the degradation of the specimen, the chromatography inspection apparatus may disadvantageously conduct an erroneous measurement.

Thus in order to solve the problem, the present invention has as its object the provision of a chromatography inspection apparatus that enables an accurate inspection by detecting degradation of a specimen during a chromatography inspection.

Means for Solving the Problems

In order to attain the object, a chromatography inspection apparatus of the present invention conducts an inspection by developing a liquid sample in the developing layer of a chromatography specimen on which a liquid-impermeable sheet material is bonded, melting a labeling reagent retained in a labeling reagent retaining part, and coloring a reagent fixing part by the labeling reagent, the chromatography inspection apparatus including: an image pickup device for imaging the chromatography specimen in a state in which the liquid sample has developed; and a measuring section for judging whether the chromatography specimen has been degraded or not based on an imaging result, wherein when the measuring section judges that the chromatography specimen has been degraded, a warning is issued.

Further, when the measuring section judges that the chromatography specimen has been degraded, an inspection operation is stopped.

Moreover, the measuring section determines, based on the imaging result, a difference in luminance between the labeling reagent retaining part and a region located downstream of the labeling reagent retaining part in the developing direction, and the measuring section judges that the chromatography specimen has been degraded when the difference is larger than a preset reference value.

Further, the measuring section determines, based on the imaging result, a difference in luminance between a region where the liquid sample has developed and a region located in the developing direction downstream of the end of the region where the liquid sample has developed, and the measuring section judges that the chromatography specimen has been degraded when the difference is smaller than the preset reference value.

Moreover, the measuring section determines, based on the imaging result, the luminance variation of the region where the liquid sample has developed, and the measuring section judges that the chromatography specimen has been degraded when the luminance variation is larger than the preset reference value.

Further, the measuring section determines, based on the imaging result, a difference in luminance between a region where the liquid-impermeable sheet material is bonded and a region located in the developing direction downstream of the end of the region where the liquid-impermeable sheet material is bonded, and the measuring section judges that the chromatography specimen has been degraded when the difference is larger than the preset reference value.

A method of judging degradation of a chromatography specimen according to the present invention, in which degradation of the chromatography specimen is detected concurrently with a chromatography inspection conducted by developing a liquid sample in the developing layer of the chromatography specimen on which a liquid-impermeable sheet material is bonded, melting a labeling reagent retained in a labeling reagent retaining part, and coloring a reagent fixing part by the labeling reagent, the method including: imaging the chromatography specimen in a state in which the liquid sample has developed; and judging whether the chromatography specimen has been degraded or not based on an imaging result, wherein when it is judged that the chromatography specimen has been degraded during the inspection, an inspection operation is stopped.

Further, the judging step includes: determining a difference in luminance between the labeling reagent retaining part and a region located downstream of the labeling reagent retaining part in the developing direction after the liquid sample has developed; and comparing the determined luminance difference with a preset reference value and judging that the chromatography specimen has been degraded when the luminance difference is larger than the reference value.

Moreover, the judging step includes: determining, after the liquid sample has developed, a difference in luminance between a region where the liquid sample has developed and a region located in the developing direction downstream of the end of the region where the liquid sample has developed; and comparing the determined luminance difference with the preset reference value and judging that the chromatography specimen has been degraded when the luminance difference is smaller than the reference value.

Further, the judging step includes: determining, after the liquid sample has developed, the luminance variation of the region where the liquid sample has developed; and comparing the luminance variation with the preset reference value and judging that the chromatography specimen has been degraded when the luminance variation is larger than the reference value.

Moreover, the judging step includes: determining, after the liquid sample has developed, a difference in luminance between a region where the liquid-impermeable sheet material is bonded and a region located in the developing direction downstream of the end of the region where the liquid-impermeable sheet material is bonded; and comparing the determined luminance difference with the preset reference value and judging that the chromatography specimen has been degraded when the luminance difference is larger than the reference value.

Advantage of the Invention

As previously mentioned, by measuring a luminance difference between predetermined two points or a luminance variation in a predetermined region in a state in which a liquid sample is developed in a chromatography specimen, and comparing the luminance difference or the luminance variation with a preset reference value, it is possible to automatically detect degradation such as a decrease in hydrophilicity in the lower portion of a liquid-impermeable sheet material during a chromatography inspection, thereby enabling an accurate inspection.

BEST MODE FOR CARRYING OUT THE INVENTION

The following will specifically describe embodiments of a chromatography inspection apparatus of the present invention in accordance with the accompanying drawings.

First Embodiment

Figure 1:
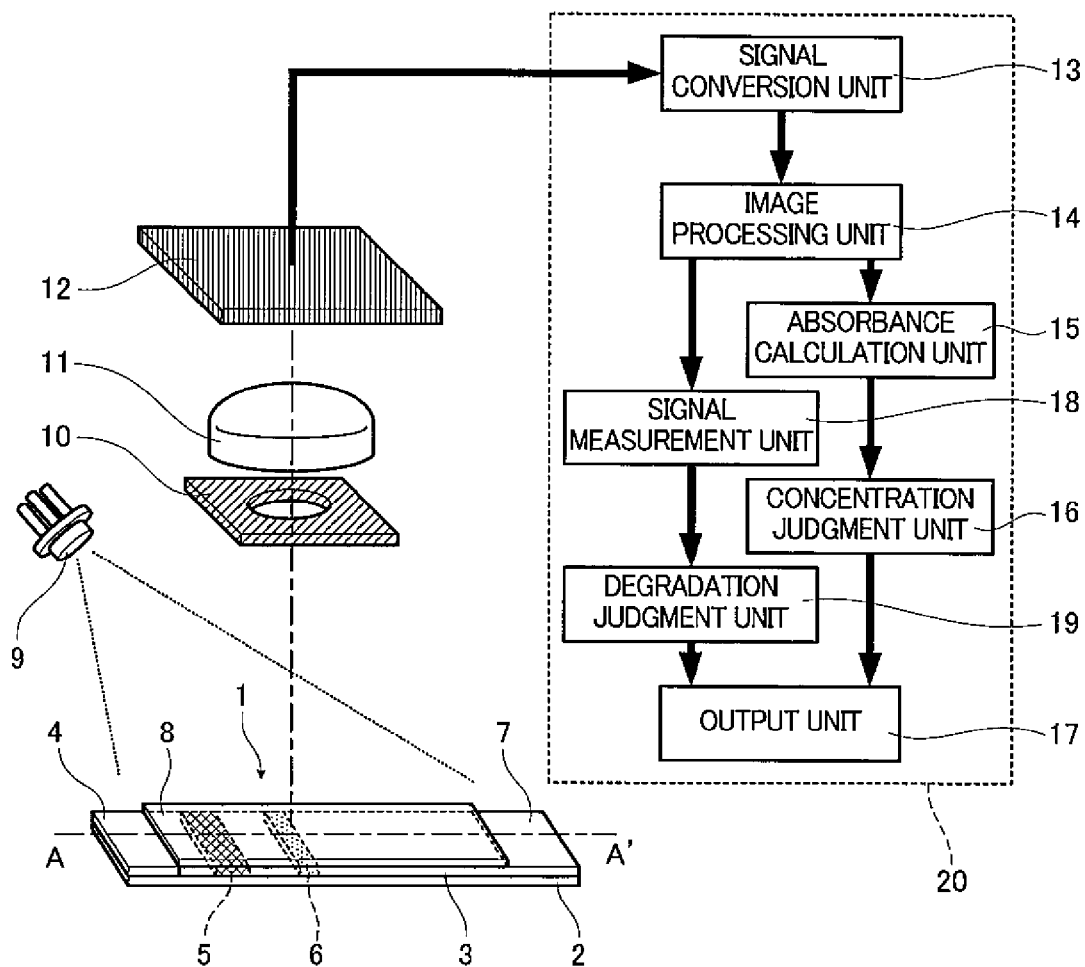
FIG. 1 is a schematic drawing showing the configurations of a specimen and a chromatography inspection apparatus for measuring a coloration result of the specimen.
Figure 2:
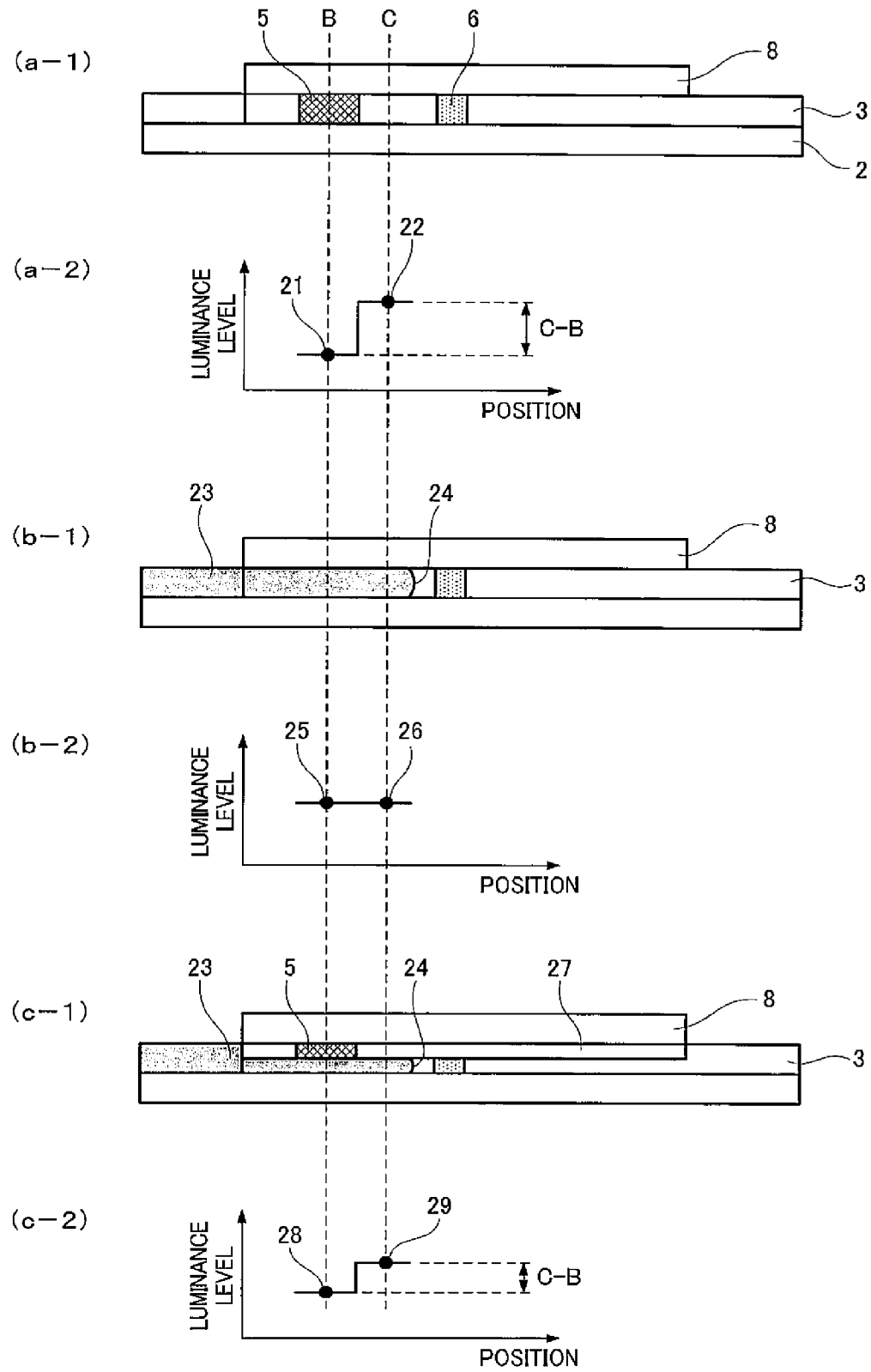
FIG. 2 is an explanatory drawing showing a method of detecting degradation in a chromatography inspection apparatus according to a first embodiment.

Referring to FIGS. 1 and 2, the following will first describe the operations of a chromatography inspection apparatus according to a first embodiment of the present invention. FIG.

1 is a schematic drawing showing the configurations of a specimen and the chromatography inspection apparatus for measuring a coloration result of the specimen.

Figure 5:
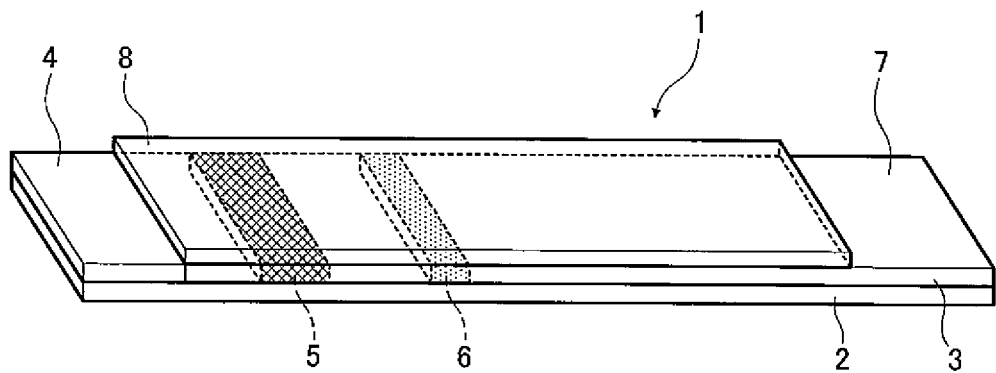
FIG. 5 is a perspective view showing the configuration of a chromatography specimen according to the prior art.

A specimen 1 has the same configuration as in FIG. 5 of the prior art and thus the explanation thereof is omitted. The chromatography inspection apparatus of FIG. 1 includes a light-emitting device 9, a diaphragm 10, a condenser lens 11, an image pickup device 12, and a measuring section 20.

The light-emitting device 9 is a lamp, a light-emitting diode, a semiconductor laser, or the like and has the function of illuminating the specimen 1. The diaphragm 10 restricts scattered light from the specimen 1. The condenser lens 11 condenses scattered light on the image pickup device 12 and forms, on a surface of the image pickup device 12, an image of a surface of the specimen 1. After that, the image pickup device 12 converts the light into an electric signal. In the measuring section 20, the electric signal from the image pickup device 12 is converted into a digital signal by a signal conversion unit 13 and image processing is performed by an image processing unit 14 such that the noise components of each pixel of the image pickup device 12 are removed and a measurement region is extracted. After the image processing, the degree of coloration of a reagent fixing part 6 is calculated as absorbance by an absorbance calculation unit 15. The absorbance is used in a concentration judgment unit 16 to calculate the concentration of a target analyte in a liquid sample according to a concentration conversion formula having been inputted to the apparatus. The concentration is displayed by an output unit 17.

In this case, the light-emitting device 9 is a light-emitting diode having a wavelength of 610 nm. The wavelength is selected under the conditions that a sufficient difference in absorbance between gold colloid (labeling reagent) and blood (liquid sample) is obtained. The following will describe the case where the labeling reagent is gold colloid and the liquid sample is blood. The same effect can be obtained also when a lamp is used as the light-emitting device 9 with a wavelength limited by an optical filter. Further, the image pickup device 12 is a CCD (Charge Coupled Device) image sensor or a CMOS (Complementary Metal Oxide Semiconductor) image sensor.

Referring to FIGS. 1 and 2, the following will describe the operations of the chromatography inspection apparatus for judging degradation of the specimen 1 (a decrease in hydrophilicity in the lower portion of a liquid-impermeable sheet material 8).

FIG. 2 is an explanatory drawing showing a method of detecting degradation in the chromatography inspection apparatus according to the first embodiment. For better understanding of the positional relationship, states of the development of the liquid sample to the specimen 1 and examples of luminance signals are vertically illustrated in the same drawing. Part (a-1), part (b-1), and part (c-1) in FIG. 2 are sectional views showing the specimen 1 of FIG. 1 along chain line A-A' of FIG. 1. Part (a-2), part (b-2), and part (c-2) in FIG. 2 schematically show the levels of the luminance signals so as to clarify a difference between point B and point C of FIG. 2, the luminance signals being obtained by the image pickup device at point B and point C. The horizontal axis indicates a position along chain line A-A' of the specimen 1 and the vertical axis indicates the level of the luminance signal. Point B and point C are located at the front and rear of the downstream end of a labeling reagent retaining part 5. Point B is located on the labeling reagent retaining part 5.

Part (a-1) of FIG. 2 shows a state in which blood (liquid sample) is not added. The liquid-impermeable sheet material 8 is in contact with the top surface of a developing layer 3, and the labeling reagent retaining part 5 and the reagent fixing part 6 are provided on the developing layer 3. At this point, as shown in part (a-2) of FIG. 2, a comparison between the levels of a luminance signal 21 at point B and a luminance signal 22 at point C proves that the level of the luminance signal 21 is extremely lower. This is because illumination light is absorbed by gold colloid (labeling reagent).

Part (b-1) of FIG. 2 shows a state in which blood (liquid sample) 23 has been added to the normal specimen 1 and then a development end (the position of the front end of the permeating liquid sample) 24 of the blood (liquid sample) 23 has passed through the labeling reagent retaining part 5 and is present in a range where the liquid-impermeable sheet material 8 is bonded. In this case, the gold colloid (labeling reagent) retained in the region of the labeling reagent retaining part 5 is completely melted by the developed blood (liquid sample) 23. Thus as shown in part (b-2) of FIG. 2, a comparison between the levels of a luminance signal 25 at point B and a luminance signal 26 at point C immediately after melting proves that the signals are substantially at the same level.

Part (c-1) of FIG. 2 shows a state in which the blood (liquid sample) 23 has been added to the degraded specimen 1 and then the development end 24 of the blood (liquid sample) 23 has passed through the labeling reagent retaining part 5 and is present in a range where the liquid-impermeable sheet material 8 is bonded. Reference numeral 27 denotes a region where an adhesive for bonding the liquid-impermeable sheet material 8 to the developing layer 3 permeates the upper portion of the developing layer 3 and hydrophilicity decreases. Because of the decrease in hydrophilicity, the blood (liquid sample) 23 added to the specimen 1 develops so as to avoid the hydrophilicity decreasing region 27. At this point, as shown in part (c-2) of FIG. 2, a comparison between the levels of a luminance signal 28 at point B and a luminance signal 29 at point C proves that the level of the luminance signal 28 is lower. This is because the blood (liquid sample) 23 does not develop in the hydrophilicity decreasing region 27 and thus does not melt the gold colloid (labeling reagent) in an overlapping portion of the labeling reagent retaining part 5 and the hydrophilicity decreasing region 27 and more illumination light is absorbed in the overlapping portion. Hence, in comparison with part (b-2) of FIG. 2, a difference in luminance level between point B and point C in part (c-2) of FIG. 2 is larger than that of part (b-2), so that degradation of the specimen 1 can be judged by detecting the difference.

According to the foregoing explanation, the chromatography inspection apparatus judges degradation of the specimen by the following operations: first, the image pickup device 12 obtains an image of the specimen 1 and converts the image into an electric signal, the signal conversion unit 13 converts the electric signal into a digital signal, and then the image processing unit 14 performs image processing for removing the noise components of each pixel of the image pickup device 12 and extracting the measurement region. After point B and point C are extracted by a signal measurement unit 18, luminance signal levels are detected at both of the points. In this case, the luminance signal level at point C is continuously monitored at time intervals having been inputted to the apparatus (about one second is desirable in practical use). When the luminance signal level falls below a level having been inputted to the apparatus, it is judged that the blood (liquid sample) 23 has developed over point C. At this point, a degradation judgment unit 19 determines a level difference between point B and point C (C-B) and compares the level difference with another reference value having been inputted to the apparatus. When the level difference is larger than the reference value, it is judged that the specimen 1 has been degraded. In this case, the time interval and the reference value that have been inputted to the apparatus may be stored in memory provided in the chromatography inspection apparatus or may be stored in memory provided in the degradation judgment unit 19. When it is judged that the specimen 1 has been degraded, the chromatography inspection apparatus issues a warning to a user through an error indication on the output unit 17 and stops the inspection operation performed on the specimen.

Thus in the chromatography inspection, luminances are measured on the labeling reagent retaining part and a portion downstream of the labeling reagent retaining part in a state in which the liquid sample has developed in the portion, and a difference in luminance level is detected. Hence, when the difference in luminance level is larger than the preset reference value, it is judged that the chromatography specimen has been degraded so as to decrease in hydrophilicity and the inspection can be stopped. It is therefore possible to automatically detect degradation of the specimen during the chromatography inspection, enabling an accurate inspection.

Second Embodiment

Figure 3:
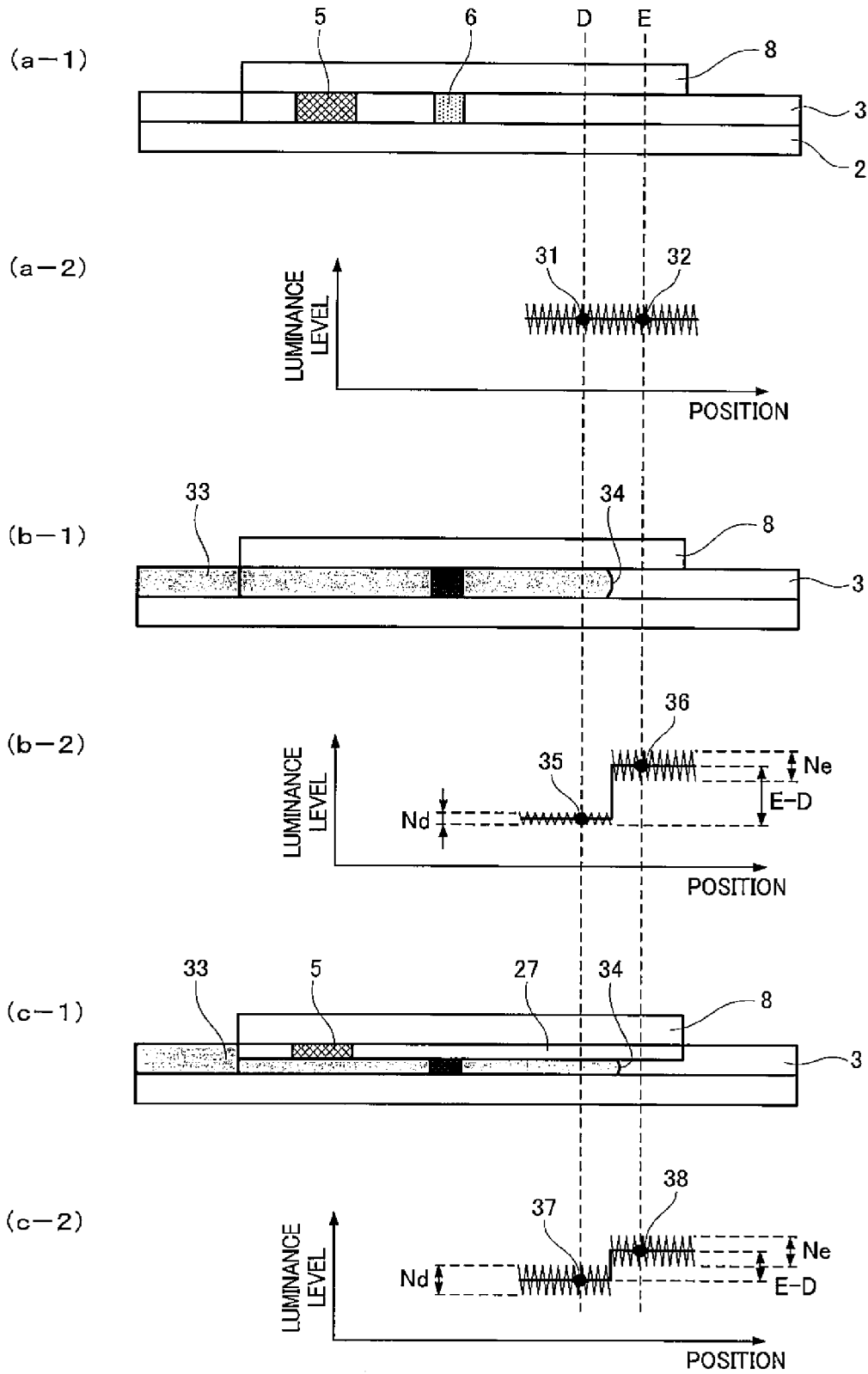
FIG. 3 is an explanatory drawing showing a method of detecting degradation in a chromatography inspection apparatus according to a second embodiment.

Referring to FIGS. 1 and 3, the operations of a chromatography inspection apparatus according to a second embodiment of the present invention will be described below. In the second embodiment, two methods of judging degradation of a specimen will be also described.

FIG. 3 is an explanatory drawing showing the method of detecting degradation in the chromatography inspection apparatus according to the second embodiment. For better understanding of the positional relationship, states of the development of blood (liquid sample) 33 to a specimen 1 and examples of luminance signals are vertically illustrated in the same drawing. Part (a-1), part (b-1), and part (c-1) in FIG. 3 are sectional views showing the specimen 1 of FIG. 1 along chain line A-A' of FIG. 1. Part (a-2), part (b-2), and part (c-2) in FIG. 3 schematically show the levels of the luminance signals so as to clarify a difference between point D and point E of FIG. 3, the luminance signals being obtained by an image pickup device at point D and point E. The horizontal axis indicates a position along chain line A-A' of the specimen 1 and the vertical axis indicates the level of the luminance signal. In this configuration, point D and point E are set in a range where a liquid-impermeable sheet material 8 is provided and are located in a region downstream of a reagent fixing part 6. Degradation is detected when the liquid sample develops to a point between point D and point E.

Part (a-1) of FIG. 3 shows a state in which the blood (liquid sample) is not added. The liquid-impermeable sheet material 8 is in contact with the top surface of a developing layer 3, and a labeling reagent retaining part 5 and the reagent fixing part 6 are provided on the developing layer 3. At this point, as shown in part (a-2) of FIG. 3, a comparison between the levels of a luminance signal 31 at point D and a luminance signal 32 at point E proves that the signals are substantially at the same level. This is because luminances in the same surface state of the developing layer 3 are compared with each other.

Part (a-2) of FIG. 3 also shows subtle changes (hereinafter called a "luminance change" and an amount of luminance change will be called a luminance variation) of the luminance signals relative to an observation position. These changes are caused by an image of unevenness on the fiber of the developing layer 3. In this image, a convex portion looks bright by illumination light and a recessed portion looks dark behind the convex portion. Although similar luminance changes are present in FIG. 2 illustrated in the first embodiment, the luminance changes are omitted in FIG. 2 for simplicity.

Part (b-1) of FIG. 3 shows a state in which the blood (liquid sample) 33 has been added to the normal specimen 1 and then the blood (liquid sample) 33 has passed through the reagent fixing part 6 and developed to the intermediate position of point D and point E. At this point, as shown in part (b-2) of FIG. 3, a comparison between the levels of a luminance signal 35 at point D and a luminance signal 36 at point E proves that the level of the luminance signal 35 is lower. This is because the blood (liquid sample) 33 containing melted gold colloid (labeling reagent) is present at point D and illumination light is absorbed at point D.

A comparison between a luminance variation Nd around the luminance signal 35 and a luminance variation Ne around the luminance signal 36 proves that Nd is smaller. This is because as previously mentioned, the developing layer 3 is dry around the luminance signal 36 and thus light and shade caused by unevenness of fiber are clearly imaged, whereas around the luminance signal 35, the fiber of the developing layer 3 is filled with the blood (liquid sample) 33 and thus the unevenness of fiber becomes less visible.

Part (c-1) of FIG. 3 shows a state in which the blood (liquid sample) 33 has been added to the degraded specimen 1 and then the blood (liquid sample) 33 has passed through the reagent fixing part 6 and developed to the intermediate position of point D and point E. Reference numeral 27 denotes a region where an adhesive for bonding the liquid-impermeable sheet material 8 to the developing layer 3 permeates the upper portion of the developing layer 3 and hydrophilicity decreases. Because of the decrease in hydrophilicity, the blood (liquid sample) 33 added to the specimen 1 develops so as to avoid the hydrophilicity decreasing region 27. At this point, as shown in part (c-2) of FIG. 3, a comparison between the levels of a luminance signal 37 at point D and a luminance signal 38 at point E proves that the level of the luminance signal 37 is lower. This is because the blood (liquid sample) 33 containing melted gold colloid (labeling reagent) is present under the hydrophilicity decreasing region 27 and thus illumination light from a light-emitting device 9 is partially absorbed by the blood (liquid sample) 33. However, in comparison with point D of part (b-2) in FIG. 3, the blood (liquid sample) 33 is not present in the hydrophilicity decreasing region 27 at point D of part (c-2) in FIG. 3 and the absorbance of illumination light decreases, accordingly. Thus degradation of the specimen 1 can be judged by detecting the difference.

Further, a comparison between a luminance variation Nd around the luminance signal 37 and a luminance variation Ne around the luminance signal 38 proves that Nd and Ne are substantially equal to each other. This is because around either of the positions of the luminance signal 37 and the luminance signal 38, a surface of the specimen 1 has the dry developing layer 3 (the hydrophilicity decreasing region 27) and light and shade caused by unevenness of fiber are clearly imaged. Thus in comparison with part (b-2) of FIG. 3, Nd of part (c-2) in FIG. 3 is larger than that of part (b-2), so that degradation of the specimen 1 can be judged by detecting the difference.

Therefore, the chromatography inspection apparatus judges degradation of the specimen 1 by the following operations:

First, in a first method, an image pickup device 12 obtains an image of the specimen 1 and converts the image into an electric signal, a signal conversion unit 13 converts the electric signal into a digital signal, and then an image processing unit 14 performs image processing for removing the noise components of each pixel of the image pickup device 12 and extracting a measurement region. After point D and point E are extracted by a signal measurement unit 18, luminance signal levels are detected at both of the points. In this case, the luminance signal level at point D is continuously monitored at time intervals having been inputted to the apparatus (about one second is desirable in practical use). When the luminance signal level falls below a level having been inputted to the apparatus, it is judged that the blood (liquid sample) 33 has developed over point D. At this point, a degradation judgment unit 19 determines a level difference between point D and point E (E-D) and compares the level difference with another reference value having been inputted to the apparatus. When the level difference is smaller than the reference value, it is judged that the specimen 1 has been degraded. In this case, the time interval and the reference value that have been inputted to the apparatus may be stored in memory provided in the chromatography inspection apparatus or may be stored in memory provided in the degradation judgment unit 19. When it is judged that the specimen 1 has been degraded, the chromatography inspection apparatus issues a warning to a user through an error indication on an output unit 17 and stops the inspection operation performed on the inspected specimen 1.

In a second method, the signal measurement unit 18 detects a luminance variation Nd at point D and the degradation judgment unit 19 compares Nd with another reference value having been inputted to the apparatus. When Nd is larger than the reference value, it is judged that the specimen 1 has been degraded. When it is judged that the specimen 1 has been degraded, the chromatography inspection apparatus issues a warning to a user through an error indication on the output unit 17 and stops the inspection operation performed on the specimen 1.

Thus in the chromatography inspection, luminances are measured in a region where the liquid sample has developed and a portion downstream of the end of the region where the liquid sample has developed, in a state in which the liquid sample develop has developed. Further, a difference in luminance level is detected. Hence, when a difference in luminance level is smaller than a preset reference value, it is judged that the chromatography specimen has been degraded so as to decrease in hydrophilicity and the inspection can be stopped. It is therefore possible to automatically detect degradation of the specimen during the chromatography inspection, enabling an accurate inspection.

The following is the supplementary explanation of the second method of the second embodiment. The present embodiment described that degradation of the specimen 1 is judged based on luminance variations along chain line A-A' on the specimen 1. Actually, it is assumed at this point that the hydrophilicity decreasing region 27 is formed over the undersurface of the liquid-impermeable sheet material 8. According to this method, however, detection is enabled also when the hydrophilicity decreasing region 27 is generated only on a part of the undersurface of the liquid-impermeable sheet material 8. In other words, after the liquid sample 33 has developed over the undersurface of the liquid-impermeable sheet material 8, the planar distribution of luminance variations in the region of the liquid-impermeable sheet material 8 is determined. When a range where a luminance variation is smaller than the reference value having been inputted to the apparatus has a total area larger than another reference value, it is judged that the specimen 1 has been degraded. According to this method, even small degradation can be judged without fail, achieving a chromatography inspection apparatus with higher reliability.

The second embodiment described that the labeling reagent retaining part 5 is disposed on the developing layer 3. Instead of this configuration, the same effect can be obtained by developing the developing layer 3 in a state in which gold colloid (labeling reagent) has been mixed with blood (liquid sample).

Third Embodiment

Figure 4:
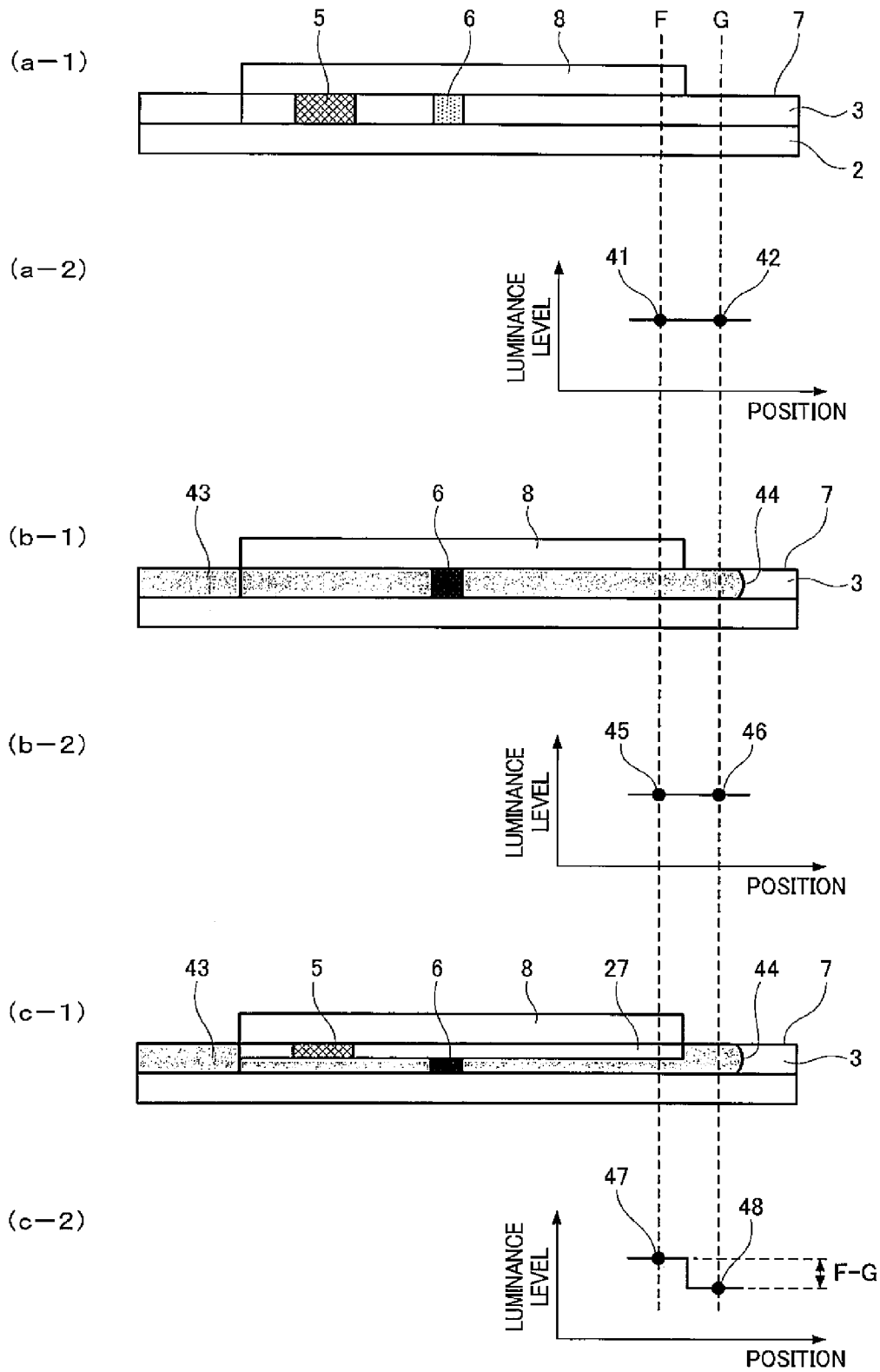
FIG. 4 is an explanatory drawing showing a method of detecting degradation in a chromatography inspection apparatus according to a third embodiment.

Referring to FIGS. 1 and 4, the operations of a chromatography inspection apparatus according to a third embodiment of the present invention will be described below.

FIG. 4 is an explanatory drawing showing a method of detecting degradation in the chromatography inspection apparatus according to the third embodiment. For better understanding of the positional relationship, states of the development of blood (liquid sample) to a specimen 1 and examples of luminance signals are vertically illustrated in the same drawing. Part (a-1), part (b-1), and part (c-1) in FIG. 4 are sectional views showing the specimen 1 of FIG. 1 along chain line A-A' of FIG. 1. Part (a-2), part (b-2), and part (c-2) in FIG. 4 schematically show the levels of the luminance signals of FIG. 4 so as to clarify a difference between point F and point G, the luminance signals being obtained by an image pickup device at point F and point G. The horizontal axis indicates a position along chain line A-A' of the specimen 1 and the vertical axis indicates the level of the luminance signal. In this configuration, points F and G are located at the front and rear of the development downstream end of a liquid-impermeable sheet material 8. Point F is located on the liquid-impermeable sheet material 8 and point G is located on a water absorbing part 7 to which the liquid-impermeable sheet material 8 is not bonded.

Part (a-1) of FIG. 4 shows a state in which the blood (liquid sample) is not added. The liquid-impermeable sheet material 8 is in contact with the top surface of a developing layer 3, and a labeling reagent retaining part 5 and a reagent fixing part 6 are provided on the developing layer 3. At this point, as shown in part (a-2) of FIG. 4, a comparison between the levels of a luminance signal 41 at point F and a luminance signal 42 at point G proves that the signals are substantially at the same level. This is because luminances in the same surface state of the developing layer 3 are compared with each other. Although FIG. 3 shows a state of a luminance change, a luminance change is omitted in FIG. 4 for simplicity.

Part (b-1) of FIG. 4 shows a state in which blood (liquid sample) 43 has been added to the normal specimen 1 and then a development end 44 of the blood (liquid sample) 43 has passed through the development downstream end of the liquid-impermeable sheet material 8 and developed to the water absorbing part 7. At this point, as shown in part (b-2) of FIG. 4, a comparison between the levels of a luminance signal 45 at point F and a luminance signal 46 at point G proves that the signals are substantially at the same level. The impermeable sheet material 8 is provided at point F but does not affect the luminance signal because of its transparency, so that luminances in the same surface state of the developing layer 3 are compared with each other.

Part (c-1) of FIG. 4 shows a state in which the blood (liquid sample) 43 has been added to the degraded specimen 1 and then the development end 44 of the blood (liquid sample) 43 has passed through the development downstream end of the liquid-impermeable sheet material 8 and developed to the water absorbing part 7. Reference numeral 27 denotes a region where an adhesive for bonding the liquid-impermeable sheet material 8 to the developing layer 3 permeates the upper portion of the developing layer 3 and hydrophilicity decreases. Because of the decrease in hydrophilicity, the blood (liquid sample) 43 added to the specimen 1 develops so as to avoid the hydrophilicity decreasing region 27. At this point, as shown in part (c-2) of FIG. 4, a comparison between the levels of a luminance signal 47 at point F and a luminance signal 48 at point G proves that the level of the luminance signal 48 is lower. This is because the impermeable sheet material 8 and the hydrophilicity decreasing region 27 are not present at point G and thus the blood (liquid sample) 43 permeates to a surface of the developing layer 3 and absorbs illumination light. Thus in comparison with part (b-2) of FIG. 4, a level difference between point F and point G is larger in part (c-2) of FIG. 4, so that degradation of the specimen 1 can be judged by detecting the difference.

According to the foregoing explanation, the chromatography inspection apparatus judges degradation of the specimen 1 by the following operations: first, an image pickup device 12 obtains an image of the specimen 1 and converts the image into an electric signal, a signal conversion unit 13 converts the electric signal into a digital signal, and then an image processing unit 14 performs image processing for removing the noise components of each pixel of the image pickup device 12 and extracting a measurement region. Further, a signal measurement unit 18 detects luminance signal levels at point F and point G. In this case, the luminance signal level at point G is continuously monitored at time intervals having been inputted to the apparatus (about one second is desirable in practical use). When the luminance signal level falls below a level having been inputted to the apparatus, it is judged that the blood (liquid sample) 43 has developed over point G. At this point, a degradation judgment unit 19 determines a level difference between point F and point G (F-G) and compares the level difference with another reference value having been inputted to the apparatus. When the level difference is larger than the reference value, it is judged that the specimen 1 has been degraded. In this case, the time interval and the reference value that have been inputted to the apparatus may be stored in memory provided in the chromatography inspection apparatus or may be stored in memory provided in the degradation judgment unit 19. When it is judged that the specimen 1 has been degraded, the chromatography inspection apparatus issues a warning to a user through an error indication on an output unit 17 and stops the inspection operation performed on the specimen 1.

Thus in the chromatography inspection, luminances are measured at the front and rear of the development downstream end of the liquid-impermeable sheet material 8 in a state in which the liquid sample has developed, and a difference in luminance level is detected. Hence, when a difference in luminance level is larger than the preset reference value, it is judged that the chromatography specimen has been degraded so as to decrease in hydrophilicity and the inspection can be stopped. It is therefore possible to automatically detect degradation of the specimen during the chromatography inspection, enabling an accurate inspection.

The third embodiment described that the labeling reagent retaining part 5 is disposed on the developing layer 3. Instead of this configuration, the same effect can be obtained by developing the developing layer 3 in a state in which gold colloid (labeling reagent) has been mixed in blood (liquid sample).

In the first to third embodiments, the specimen sample is a blood sample. Other samples such as urine, saliva, and body fluid can be used without any trouble.

Further, the first to third embodiments described the apparatus for detecting a reduction in the hydrophilicity of the developing layer. The hydrophilicity is reduced by the permeating adhesive of the liquid-impermeable sheet material. The apparatus is also applicable to a similar hydrophilicity decreasing region generated by another member or reagent.

The first to third embodiments described the use of the signals obtained by imaging the specimen 1 with the image pickup device. The present invention is similarly applicable to the case where illumination light is condensed and is emitted to the specimen 1 and a change of scattered light amount is used as a signal when the illumination light and the specimen 1 are relatively moved.

INDUSTRIAL APPLICABILITY

A measuring method of the present invention is applicable as a measuring method using a biosensor for quickly analyzing a biological sample with high reliability and measuring accuracy.

The invention claimed is:

1. A chromatography inspection apparatus for conducting an inspection by developing a liquid sample in a developing layer of a chromatography specimen on which is a liquid-impermeable sheet material is bonded, melting a labeling reagent retained in a labeling reagent retaining part, and coloring a reagent fixing part by the labeling reagent, the chromatography inspection apparatus comprising:

an image pickup device for imaging the chromatography specimen in a state in which the liquid sample has developed; and a measuring section for judging whether the chromatography specimen has been degraded or not based on an imaging result, wherein when the measuring section judges that the chromatography specimen has been degraded, a warning is issued, and wherein the measuring section determines, based on the imaging result, a difference in luminance between the labeling reagent retaining part and a region located downstream of the labeling reagent retaining part in a developing direction, and the measuring section judges that the chromatography specimen has been degraded when the difference is larger than a preset reference value.

2. The chromatography inspection apparatus according to claim 1, wherein when the measuring section judges that the chromatography specimen has been degraded, an inspection operation is stopped.

3. A chromatography inspection apparatus for conducting an inspection by developing a liquid sample in a developing layer of a chromatography specimen on which a liquid-impermeable sheet material is bonded, melting a labeling reagent retained in a labeling reagent retaining part, and coloring a reagent fixing part by the labeling reagent, the chromatography inspection apparatus comprising:

an image pickup device for imaging the chromatography specimen in a state in which the liquid sample has developed; and a measuring section for judging whether the chromatography specimen has been degraded or not based on an imaging result, wherein when the measuring section judges that the chromatography specimen has been degraded, a warning is issued, and wherein the measuring section determines, based on the imaging result, a difference in luminance between a region where the liquid sample has developed and a region located in a developing direction downstream of an end of the region where the liquid sample has developed, and the measuring section judges that the chromatography specimen has been degraded when the difference is smaller than a preset reference value.

4. The chromatography inspection apparatus according to claim 3, wherein when the measuring section judges that the chromatography specimen has been degraded, an inspection operation is stopped.

5. A chromatography inspection apparatus of conducting an inspection by developing a liquid sample in a developing layer of a chromatography specimen on which a liquid-impermeable sheet material is bonded, melting a labeling reagent retained in a labeling reagent retaining part, and coloring a reagent fixing part by the labeling reagent, the chromatography inspection apparatus comprising:
an image pickup device for imaging the chromatography specimen in a state in which the liquid sample has developed; and
a measuring section for judging, based on an imaging result, whether the chromatography specimen has been degraded by a decrease in hydrophilicity of a portion of the developing layer of the chromatography specimen contacting the liquid-impermeable sheet material or not,
wherein when the measuring section judges that the chromatography specimen has been degraded, a warning is issued, and
wherein the measuring section determines, based on the imaging result, a difference in luminance between a region where the liquid-impermeable sheet material is bonded and a region located in a developing direction downstream of a downstream end of the region where the liquid-impermeable sheet material is bonded, and the measuring section judges that the chromatography specimen has been degraded by the decrease in hydrophilicity of the developing layer of the chromatography specimen when the difference is larger than a preset reference value.

6. A method of judging degradation of a chromatography specimen, in which degradation of the chromatography specimen is detected concurrently with a chromatography inspection conducted by developing a liquid sample in a developing layer of the chromatography specimen on which a liquid-impermeable sheet material is bonded, melting a labeling reagent retained in a labeling reagent retaining part, and coloring a reagent fixing part by the labeling agent, the method comprising:
imaging the chromatography specimen in a state in which the liquid sample has developed; and
judging whether the chromatography specimen has been degraded or not based on an imaging result,
wherein when it is judged that the chromatography specimen has been degraded during the inspection, an inspection operation is stopped, and
wherein the judging step comprises:
determining a difference in luminance between the labeling reagent retaining part and a region located downstream of the labeling reagent retaining part in a developing direction after the liquid sample has developed; and
comparing the determined luminance difference with a preset reference value and judging that the chromatography specimen has been degraded when the luminance difference is larger than the reference value.

7. A method of judging degradation of a chromatography specimen, in which degradation of the chromatography specimen is detected concurrently with a chromatography inspection conducted by developing a liquid sample in a developing layer of the chromatography specimen on which a liquid-impermeable sheet material is bonded, melting a labeling reagent retained in a labeling reagent retaining part, and coloring a reagent fixing part by the labeling agent, the method comprising:
imaging the chromatography specimen in a state in which the liquid sample has developed; and
judging whether the chromatography specimen has been degraded or not based on an imaging result,
wherein when it is judged that the chromatography specimen has been degraded during the inspection, an inspection operation is stopped, and
wherein the judging step comprises:
determining, after the liquid sample has developed, a difference in luminance between a region where the liquid sample has developed and a region located in a developing direction downstream of an end of the region where the liquid sample has developed; and
comparing the determined luminance difference with a preset reference value and judging that the chromatography specimen has been degraded when the luminance difference is smaller than the reference value.

8. A method of judging degradation of a chromatography specimen, in which degradation of the chromatography specimen is detected concurrently with a chromatography inspection conducted by developing a liquid sample in a developing layer of the chromatography specimen on which a liquid-impermeable sheet material is bonded, melting a labeling reagent retained in a labeling reagent retaining part, and coloring a reagent fixing part by the labeling agent, the method comprising:
imaging the chromatography specimen in a state in which the liquid sample has developed; and
judging, based on an imaging result, whether the chromatography specimen has been degraded by a decrease in hydrophilicity of a portion of the developing layer of the chromatography specimen contacting the liquid-impermeable sheet material or not,
wherein when it is judged that the chromatography specimen has been degraded during the inspection, an inspection operation is stopped, and
wherein the judging step comprises:
determining, after the liquid sample has developed, a difference in luminance between a region where the liquid-impermeable sheet material is bonded and a region located in a developing direction downstream of a downstream end of the region where the liquid-impermeable sheet material is bonded; and
comparing the determined luminance difference with a preset reference value and judging that the chromatography specimen has been degraded by the decrease in hydrophilicity of the developing layer of the chromatography specimen when the luminance difference is larger than the reference value.

* * * * *